United States Patent
Ingimarsson

(10) Patent No.: US 9,707,107 B2
(45) Date of Patent: *Jul. 18, 2017

(54) PROSTHETIC PIN LOCKING MECHANISM WITH VACUUM TUNNELS

(71) Applicant: OSSUR HF, Reykjavik (IS)

(72) Inventor: Gudni Ingimarsson, Reykjavik (IS)

(73) Assignee: OSSUR HF, Reykjavik (IS)

(*) Notice: Subject to any disclaimer, the term of this patent is extended or adjusted under 35 U.S.C. 154(b) by 0 days.

This patent is subject to a terminal disclaimer.

(21) Appl. No.: 15/204,772

(22) Filed: Jul. 7, 2016

(65) Prior Publication Data

US 2016/0317327 A1    Nov. 3, 2016

Related U.S. Application Data

(63) Continuation of application No. 14/321,379, filed on Jul. 1, 2014, now Pat. No. 9,408,725.

(60) Provisional application No. 61/842,665, filed on Jul. 3, 2013.

(51) Int. Cl.
*A61F 2/80* (2006.01)
*A61F 2/78* (2006.01)

(52) U.S. Cl.
CPC ............ *A61F 2/80* (2013.01); *A61F 2/78* (2013.01); *A61F 2002/7875* (2013.01); *A61F 2002/802* (2013.01); *A61F 2002/805* (2013.01)

(58) Field of Classification Search
CPC .............. A61F 2/80; A61F 2002/7875; A61F 2002/802; A61F 2002/805; A61F 2002/807
See application file for complete search history.

(56) References Cited

U.S. PATENT DOCUMENTS

| | | |
|---|---|---|
| 5,888,234 A | 3/1999 | Littig |
| 6,063,125 A | 5/2000 | Arbogast et al. |
| 6,136,039 A | 10/2000 | Kristinsson et al. |
| 6,334,876 B1 | 1/2002 | Perkins |
| 6,605,118 B2 | 8/2003 | Capper et al. |
| 6,626,952 B2 | 9/2003 | Janusson et al. |
| 6,926,742 B2 | 8/2005 | Caspers et al. |
| 7,118,602 B2 | 10/2006 | Bjarnason |
| 7,427,298 B1 | 9/2008 | Swanson, Sr. |
| 7,438,843 B2 | 10/2008 | Asgeirsson |
| 7,927,377 B2 * | 4/2011 | Slemker ............ A61F 2/78 623/34 |

(Continued)

FOREIGN PATENT DOCUMENTS

| | | |
|---|---|---|
| DE | 102011116280 A1 | 4/2013 |
| WO | 84/00881 A1 | 3/1984 |

OTHER PUBLICATIONS

International Search Report from Corresponding International Application No. PCT/US2014/045058, Oct. 6, 2014.

*Primary Examiner* — Bruce E Snow
(74) *Attorney, Agent, or Firm* — Workman Nydegger

(57) ABSTRACT

A pin lock for a prosthetic device in a vacuum assisted suspension system includes a pin defining a longitudinally elongate bore and at least one passageway extending obliquely relative to the bore and communicating therewith at a proximal end of the pin. The pin lock also includes a locking mechanism having a receiving port arranged to receive the pin and a channel located at a distal end of the receiving port and adapted to communicate with the bore to exhaust air through the pin therefrom.

19 Claims, 7 Drawing Sheets

(56) References Cited

U.S. PATENT DOCUMENTS

| | | |
|---|---|---|
| 8,097,043 B2 | 1/2012 | Egilsson |
| 8,182,547 B2 | 5/2012 | King |
| 8,211,187 B2 | 7/2012 | Slemker et al. |
| 2011/0022183 A1 | 1/2011 | Slemker et al. |
| 2011/0307080 A1 | 12/2011 | Perkins et al. |
| 2012/0109336 A1 | 5/2012 | Laghi |
| 2013/0289742 A1 | 10/2013 | Halldorsson et al. |

* cited by examiner

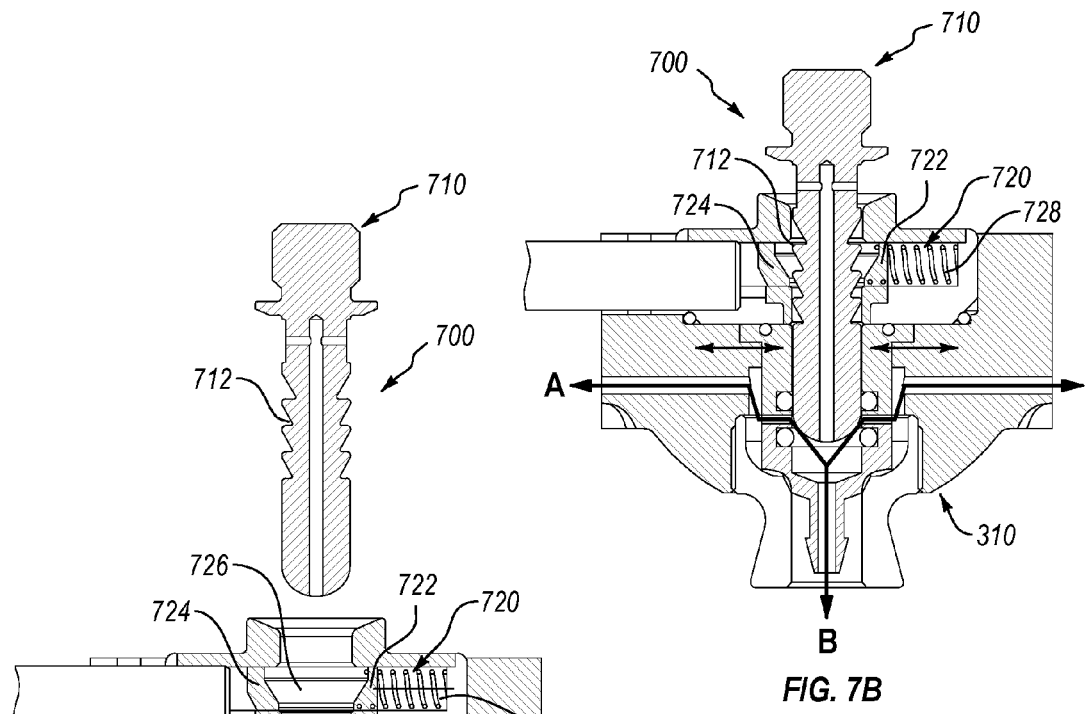
FIG. 7A
FIG. 7B
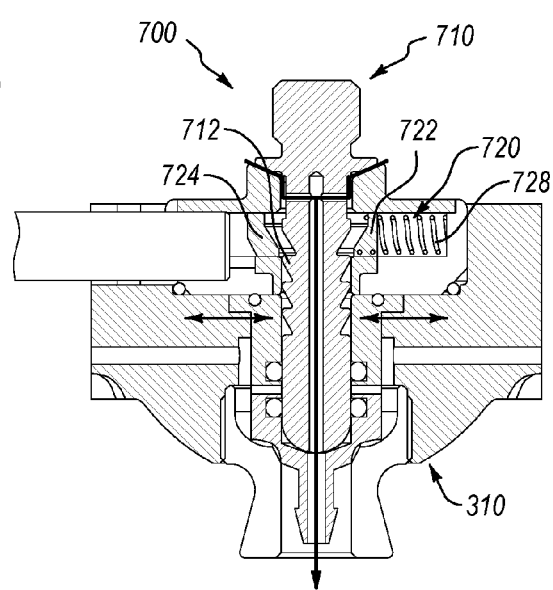
FIG. 7C

PROSTHETIC PIN LOCKING MECHANISM WITH VACUUM TUNNELS

FIELD OF ART

The disclosure relates to the field of prosthetic devices, and more particularly to a prosthetic device, system and method for increasing vacuum in a vacuum assisted suspension system.

BACKGROUND

With advancements in prosthetic components, improved suspension solutions have become a pressing need. Elevated vacuum suspension has been around for nearly a decade, and improves proprioception and volume control. The concept is well accepted and has gained many users.

A vacuum in the sense of elevated vacuum solutions refers to creating pressure significantly lower than atmospheric pressure. In prosthetic systems, a vacuum is not applied directly to the skin, but typically between the hard socket and the skin interface. The vacuum system is adapted to stabilize soft tissue volume at the residuum that the liner and hard socket surround and maintain more effective suspension of a prosthetic system.

A significant drawback to known elevated vacuum solutions is they fail to adapt to limb volume change which occurs particularly when a user is walking. Yet another drawback is that in some cases a vacuum formed at the bottom of a tight socket can suck a residual limb into the socket during donning causing various skin and soft tissue problems with the limb.

Accordingly, there is a need for a prosthetic device, system and method that provides an elevated vacuum solution that adapts to a residual limb during normal use. There is also a call to provide an elevated vacuum solution that does not present a danger of sucking a residual limb into the socket during donning. There is a demand for safely applying a vacuum where it is needed, while still stabilizing volume and maintaining vacuum suspension.

SUMMARY

In an embodiment of a pin lock for a prosthetic device in a vacuum assisted suspension system, the pin lock includes a pin defining a longitudinally elongate bore and at least one passageway extending obliquely relative to the bore and communicating therewith at a proximal end of the pin. The pin lock also includes a locking mechanism having a receiving port arranged to receive the pin and a channel located at a distal end of the receiving port and adapted to communicate with the bore to exhaust air through the pin therefrom.

The pin may define an annular flange protruding from a proximal area and a shaft extending distally from the annular flange. The bore is formed concentric with the shaft. The annular flange may be arranged to rest against the locking mechanism when the shaft is fully received by the receiving port. The annular flange may be located proximally to the at least one passageway. The receiving port may define a conical opening narrowing distally toward an elongate cavity adapted to closely receive shaft. The annular flange may have an edge profile adapted to correspondingly mate with a surface of the receiving port defining the conical opening.

The receiving port may define an elongate cavity adapted to closely receive the shaft. The locking mechanism may include a first seal protruding inwardly into the cavity from a side wall defining the cavity and adapted to engage an outer surface of the shaft. A second seal protrudes inwardly into the cavity from the side wall and is adapted to engage the outer surface of the shaft. The second seal is located proximally to the first seal and spaced a distance apart from the first seal.

The locking mechanism may form at least one release port located along the cavity and communicate to exterior of the locking mechanism to expel air therefrom. The at least one release port may extend generally perpendicularly to a longitudinal length of the cavity. The receiving port may define an elongate cavity adapted to closely receive the shaft. The first is adapted to engage an outer surface of the shaft and is located distally to the at least one release port. The second seal may be located proximally to the first seal and spaced a distance apart from the first seal and at least one release port.

The at least one passageway may generally extend perpendicular to the bore. An outer surface of the shaft may be substantially smooth.

Alternative means may be provided to prevent withdrawal of the pin from the locking mechanism, and such means may include a rack and pinion device or a ratchet device, whereby both the pin and locking mechanism have features permitting selective engagement with one another.

A method for expelling air in a prosthetic device with a vacuum assisted suspension system includes providing the prosthetic device with a suspension liner carrying a pin at a distal end and a socket. The suspension liner is placed into the socket and the pin is oriented with the receiving port. The pin is inserted into the receiving port such that air between the socket and the suspension liner is expelled at least through the passageway into the bore and through the channel to an exterior of the locking mechanism.

The method may further include resting the annular flange at a proximal area above the at least one passageway against a proximal end of the locking mechanism when the pin is fully received by the receiving port. An outer surface of the pin may be sealed against the side wall defining the cavity of the receiving port. First and second seals may protruding inwardly into the cavity and engage the outer surface of the shaft. Air may be expelled from a side wall via the at least one port as the pin is inserted into the cavity.

BRIEF DESCRIPTION OF THE DRAWINGS

The prosthetic device is described referring to the accompanying drawings which show preferred embodiments according to the device described. The device, system and method as disclosed in the accompanying drawings are illustrated for example only. The elements and combinations of elements described below and illustrated in the drawings can be arranged and organized differently to result in embodiments still within the spirit and scope of the device described.

FIGS. 7A-7C show another embodiment of the prosthetic device and installation thereof.

DETAILED DESCRIPTION OF VARIOUS EMBODIMENTS

Figure 1:
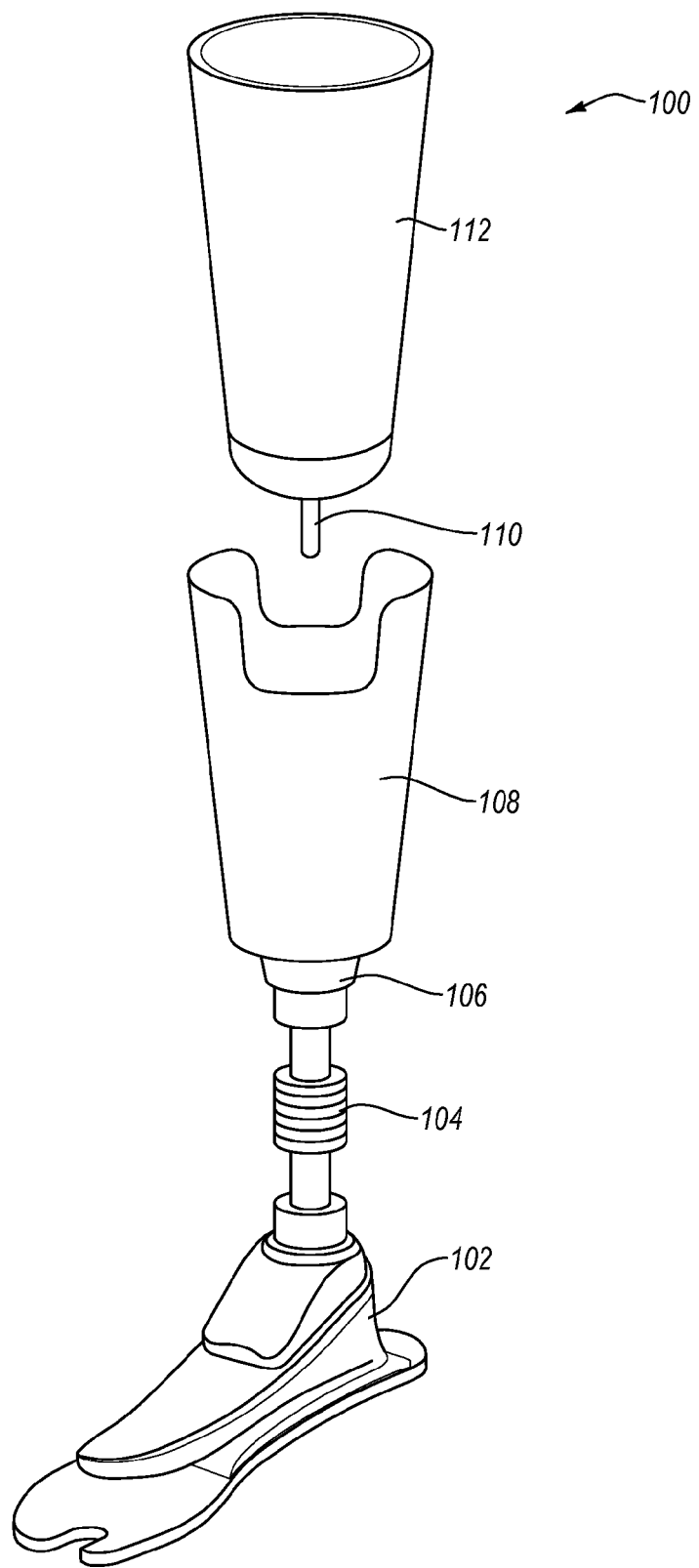
FIG. 1 shows a front view of an embodiment of the prosthetic device.

A better understanding of different embodiments of the prosthetic device may be gained from the following description read with the accompanying drawings in which like reference characters refer to like elements.

While the disclosure is susceptible to various modifications and alternative constructions, certain illustrative embodiments are in the drawings and will be described below. It should be understood, however, there is no intention to limit the disclosure to the specific embodiments disclosed, but on the contrary, the intention covers all modifications, alternative constructions, combinations, and equivalents falling within the spirit and scope of the disclosure and defined by the appended claims.

It will be understood that, unless a term is expressly defined in this disclosure to possess a described meaning, there is no intent to limit the meaning of such term, either expressly or indirectly, beyond its plain or ordinary meaning.

Any element in a claim that does not explicitly state "means for" performing a specified function, or "step for" performing a specific function, is not to be interpreted as a "means" or "step" clause as specified in 35 U.S.C. § 112, paragraph 6.

FIG. 1 illustrates an embodiment of the prosthetic pin locking pin lock 106 incorporated into a prosthetic device 100 including a socket and a liner. The embodiments described herein may be adapted as a prosthetic liner, for example, a cushion liner, which forms an interface between the skin of a residual limb and preferably a rigid or semi-rigid socket. The prosthetic liner stabilizes soft tissues, minimizes pistoning (stretching), helps to improve circulation, and adds comfort.

A liner 112 is to be rolled onto a residual limb (not shown) of an amputee. Typical liners are made of soft, stretchy material, such as silicone, and protect the limb and act as an interface between a hard, weight bearing socket 108 and the skin of the limb.

An example of a socket, as is readily understood by the skilled artisan in the field of prosthetics, is described in U.S. Pat. No. 7,438,843, granted Oct. 21, 2008, the entirety of which is incorporated herein by reference. The liner may be formed in accordance with any of the following U.S. Pat. No. 6,136,039, granted Oct. 24, 2000, U.S. Pat. No. 6,626,952, granted Sep. 30, 2003, and U.S. Pat. No. 7,118,602, granted Oct. 10, 2006, each of which are incorporated herein by reference in their entirety.

A pin 110 is secured to a distal end of the liner 112. The pin 110 may be mounted to the liner 112 by being molded or screwed into a distal end of the liner. The distal end of the liner 112 may comprise additional padding or an increased thickness of material to protect the residual limb from any hard and/or sharp edges on the pin 110.

Figure 2:
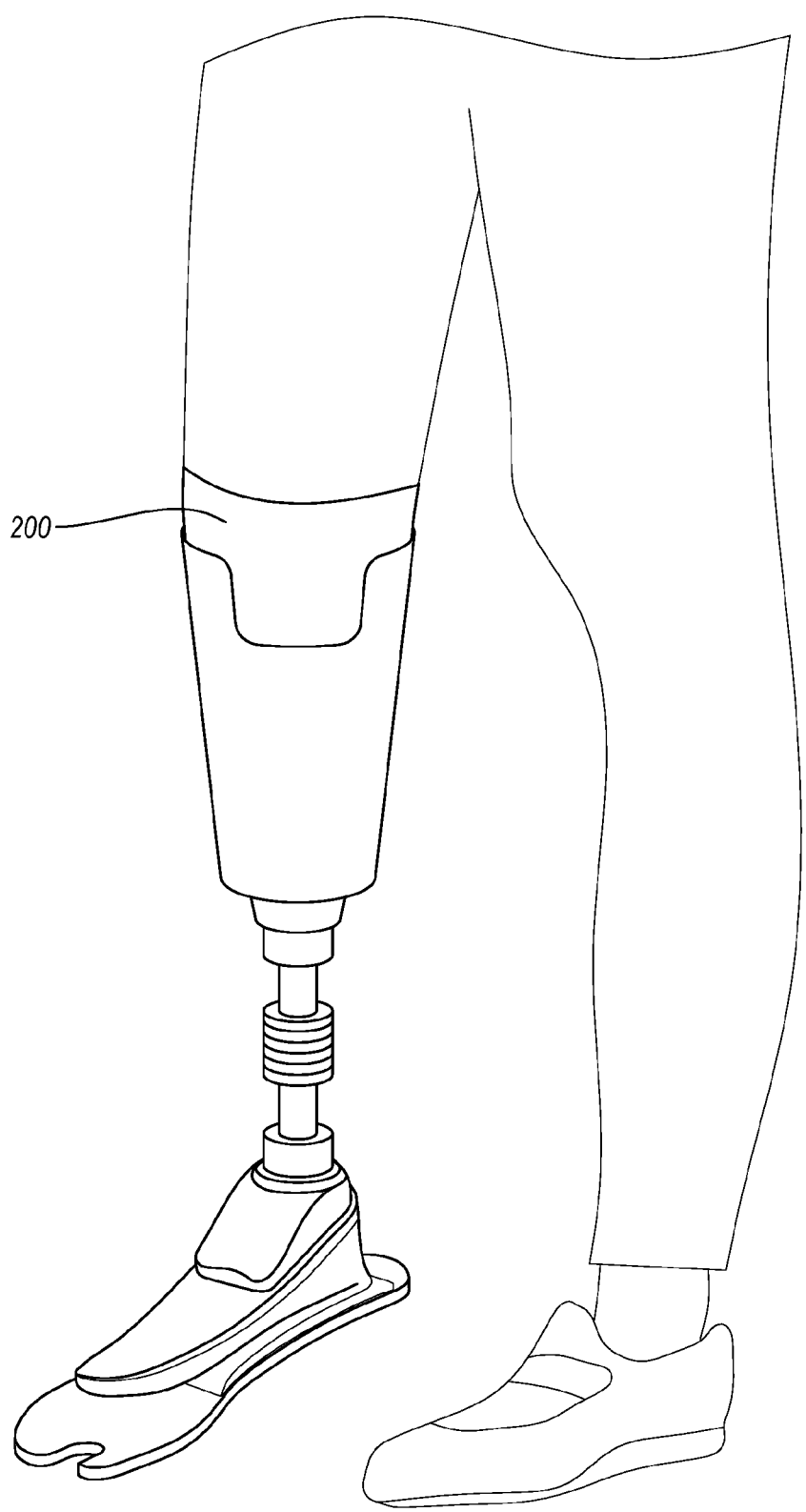
FIG. 2 shows another front view of an embodiment of the prosthetic device.

The prosthetic device 100 also includes a prosthetic foot 102 and a connection element 104, such as a pylon. FIG. 2 shows another front view of an embodiment of the prosthetic device 100 including a prosthetic sleeve 200. In some embodiments, a prosthetic sleeve 200 can create a seal between the socket 108 and the liner 112, as disclosed in U.S. Pat. No. 8,097,043 granted Jan. 17, 2012 and incorporated herein by reference in its entirety. Other embodiments may use a variety of different methods and systems for creating a seal. For example, a socket may comprise a built-in internal seal such that a sleeve 200 is not required to create a seal.

The importance of creating a vacuum within the socket 108 is well known in the art. In particular, it is understood that a vacuum creates a tighter suspension and increased proprioception. To this end, in at least one embodiment, a prosthetic device 100 can also include a vacuum pump (not shown) to create an elevated vacuum within the socket 108. An elevated vacuum is created by a system that generates a vacuum within the socket 108 that is significantly below atmospheric pressure. An example of a vacuum system is described in U.S. Appl. Pub. No. 2013/0289742 published on Oct. 31, 2013 and incorporated herein by reference in its entirety.

Figure 3:
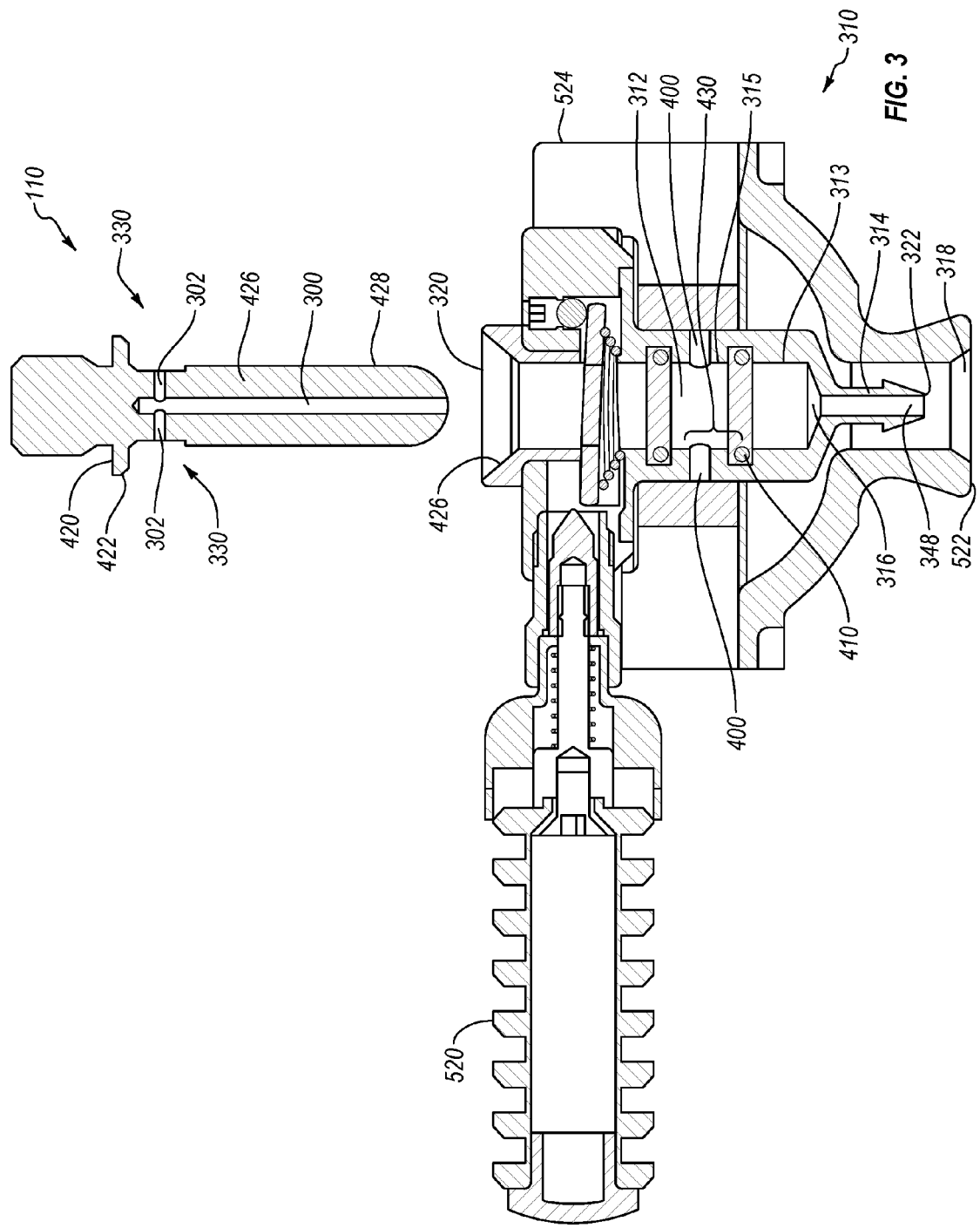
FIG. 3 shows an embodiment of the pin locking mechanism.
Figure 4:
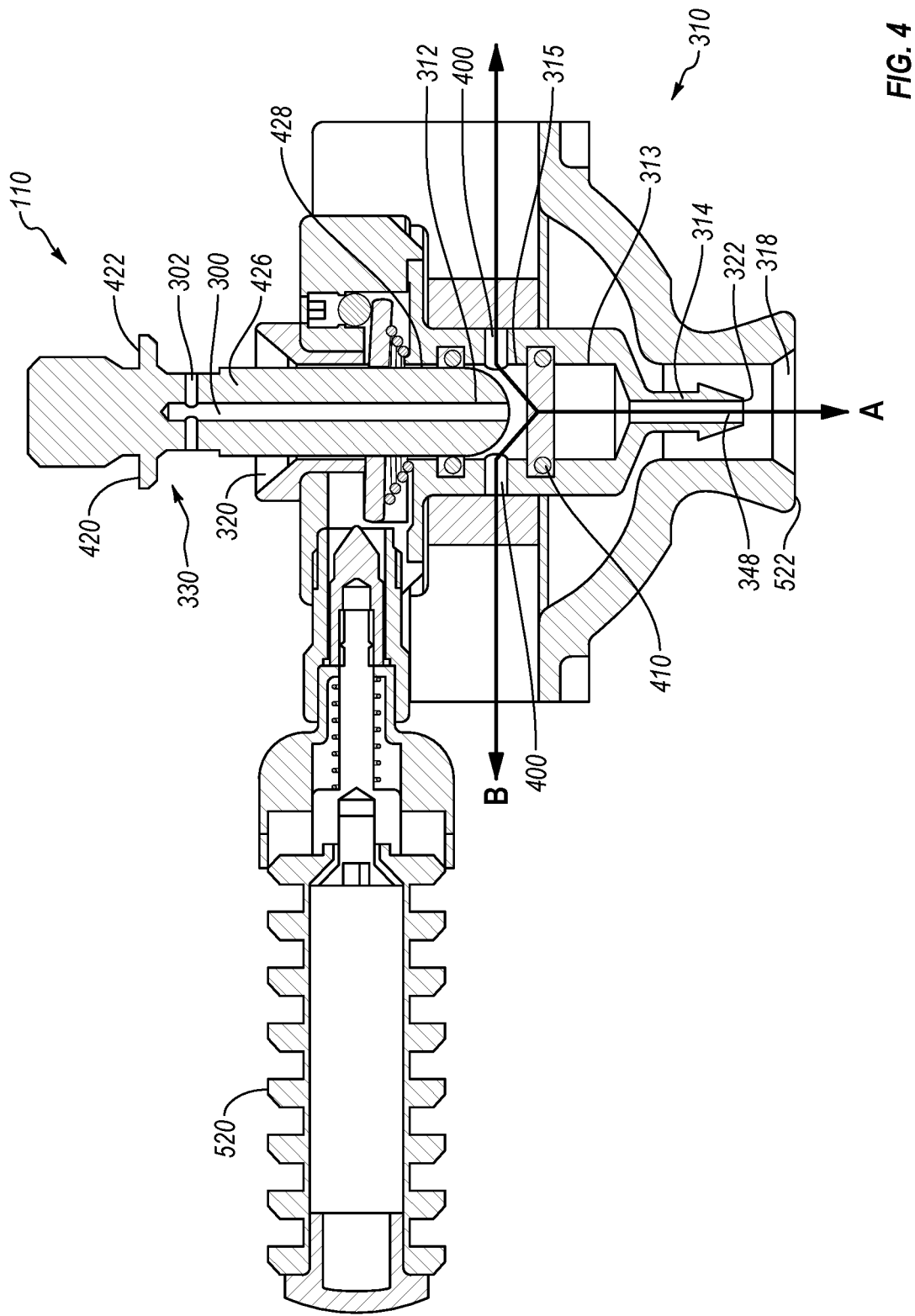
FIG. 4 shows an embodiment of the plunger being inserted into a locking mechanism.
Figure 5:
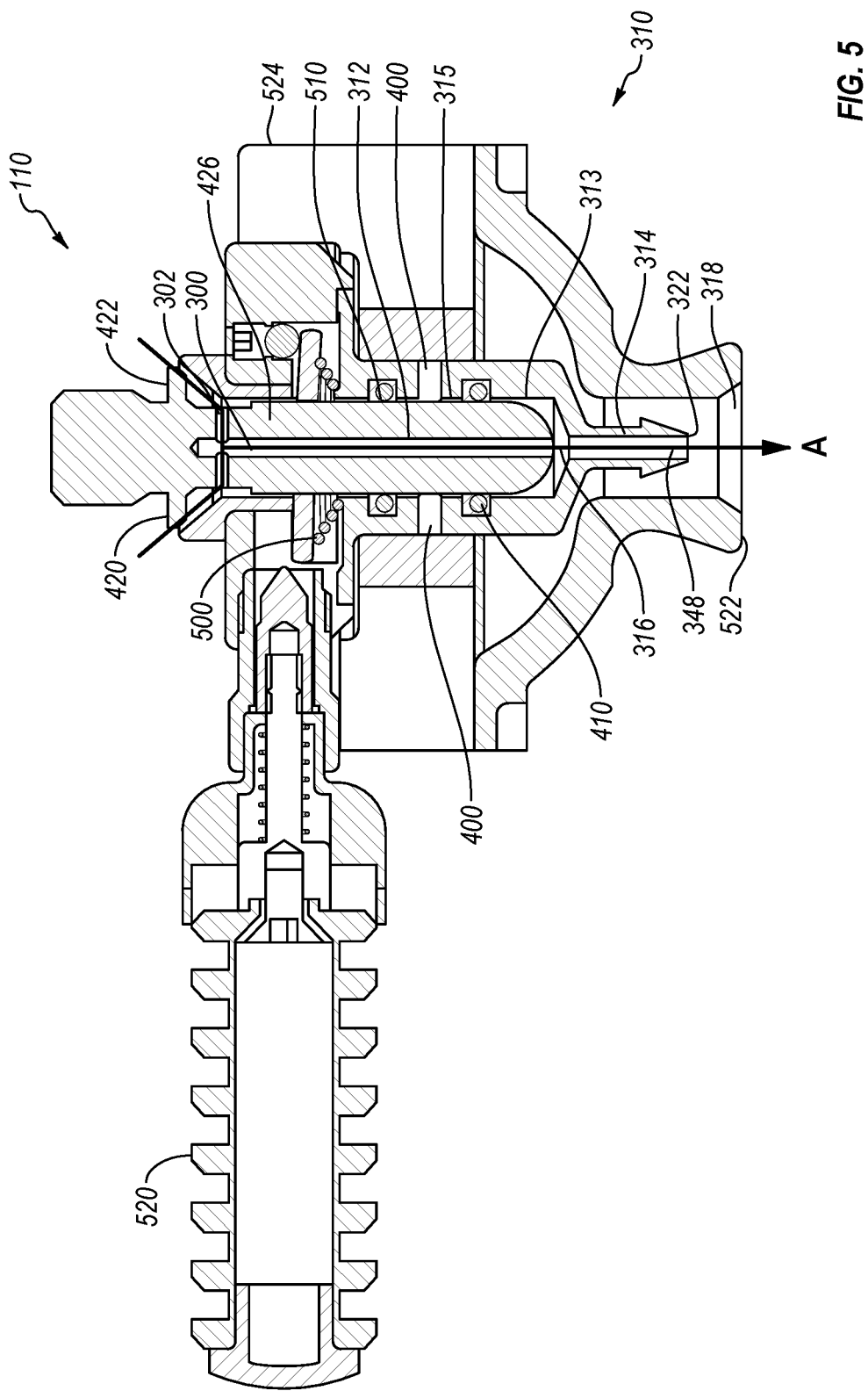
FIG. 5 shows the plunger completely inserted into the locking mechanism.

FIGS. 3-5 depicts an embodiment of a pin lock 106 for use in a vacuum assisted suspension system. The pin lock 106 includes a pin 110 defining a longitudinally elongate bore 300 and at least one passageway 302 extending obliquely relative to the bore 300 and communicating therewith at a proximal end of the pin 110. A locking mechanism 310 has a receiving port 312 arranged to receive the pin 110 and a channel 314 located at a distal end of the receiving port 312 and adapted to communicate with the bore 300 to exhaust air through the pin 110 therefrom. The at least one passageway 302 may generally extend perpendicular to the bore 300.

In a variation, the passageway 302 may not extend through the pin, but rather may be formed as channels extending along the peripheral surface of the pin, or yet another variation the passageway may only extend partially through the pin. In yet another alternative, the channels may be formed as a combination of the aforementioned possibilities.

A vacuum device communicates with the internal bore 300 to establish an elevated vacuum within the prosthetic device 100. The internal bore 300 can be in communication with the at least one intake passageway 302, located on a proximal end of the pin 110. The at least one passageway 302 can connect the internal bore 300 to an exterior of the pin 110 (i.e., an interior of the socket 108).

The at least one passageway 302 on the pin 110 may also be disposed within an inset portion 330 of the pin 110. The inset portion 330 may provide a space between the pin 110 and the receiving port 312 when the pin 110 is completely inserted into the receiving port 312. In particular, the inset portion 330 may allow a vacuum device to draw air out and allow the socket 108 even when then pin 110 is disposed within the receiving port 312 to such a depth that the at least one passageway 302 is completely disposed within the receiving port 312.

The pin 110 defines an annular flange 420 protruding from a proximal area and a shaft 426 extending distally from the annular flange 420. The bore is 300 is formed concentric with the shaft 426. The annular flange 420 is arranged to rest against the locking mechanism 310 when the shaft 426 is fully received by the receiving port 312. The annular flange 420 is located proximally to the at least one passageway 302. An outer surface 428 of the shaft 426 is substantially smooth.

A distal portion of the receiving port 312 can comprise a channel 314 preferably defining a channel 316 for communicating with a vacuum device. The channels 314, 316 can provide an interface for a variety of different types of vacuum devices to connect to the prosthetic device 100. Connecting a vacuum device to the channel 314 can cause at least some level of suction to be applied to the internal bore 300 when the pin 110 is inserted into the receiving port 312. An aim of the present disclosure is to apply the vacuum force (i.e., suction) to the inside of the socket 108.

In at least one embodiment, however, the receiving port 312 comprises at least one release port 400 that prevents the vacuum from being applied to the inside of the socket 108 until the pin 110 is nearly completely inserted into the receiving port 312. For example, FIG. 4 shows the vacuum forces being diverted from the internal bore 300 of the pin 110, and in turn the inside of the socket 108, by two vacuum release ports 400. The at least one release port 400 can be in communication with air external to the prosthetic device 100 such that no vacuum can be formed by the vacuum forces acting upon the at least one release port 400. The at least one release port 400 may extend generally perpendicularly to a longitudinal length of an elongate cavity 313 adapted to closely receive shaft 426.

As depicted in FIG. 4, air (A) is expelled from an orifice 318 at the distal end 322 of the vacuum connector 314 and out from the locking mechanism. The distal end 322 may define a peripheral connector 522, such as a pyramidal connector. Air (B) is expelled from the at least one release port 400 as the pin 110 is inserted into the cavity 313.

The locking mechanism 310 includes a first seal 410 protruding inwardly into the cavity 313 from a side wall 315 defining the cavity 313 and is adapted to engage an outer surface 428 of the shaft 426. The first seal 410 is sized and shaped to seal around the pin 110 when the pin 110 is inserted sufficiently far into the cavity 313 of the receiving port 312. The first seal 410 can be positioned between the vacuum device connector 314 and the vacuum release ports 400 such that the first seal 410 can isolate the channel 314 from the vacuum release ports 400 when the pin 110 is inserted.

FIG. 5 shows the pin 110 completely inserted into the receiving port 312 of the locking mechanism 310. As explained above, once the pin 110 is sufficiently inserted into the receiving port 312, the pin 110 and the first seal 410 can isolate the channel 314 from the vacuum release ports 400. Once the vacuum release ports 400 are isolated from the channel 314, the vacuum force can be applied to the internal bore 300 of the pin 110 and thus to the inside of the socket 108.

A second seal 510 protrudes inwardly into the cavity 313 from the side wall 315 and is adapted to engage the outer surface 428 of the shaft 426. The second seal 510 is located proximally to the first seal 410 and spaced a distance 430 apart from the first seal 313.

The second seal 510 can serve the function of creating a seal between the interior of the socket 108 and the vacuum release ports 400. The second seal 510 may aid in preventing a vacuum from escaping from the interior of the socket 108 and exiting through any gap between the top of the receiving port and the pin 110 and escaping out the vacuum release port 400.

As depicted in FIGS. 3-5, the first component seal 410 and the second component seal 510 comprise O-rings. However, in other embodiments the first component seal 410 and/or the second component seal 510 can comprise a variety of different sealing mechanisms. For example, the first component seal 410 and/or the second components seal 510 can comprise a press fit seal, wherein the fit between the pin 110 and the receiving port 312 is so tight that a mechanical seal is automatically created when the pin 110 is inserted into the receiving port 312. Regardless of the seal type, in at least one implementation, the seal can prevent a vacuum from being applied to the socket 108 before the pin 110, and by association, the wearer's residual limb, is nearly completely inserted.

At least one advantage of not applying a vacuum force to the socket 108 until the pin 110 is nearly completely inserted into the receiving port 312 is that it lessens the danger of sucking a residual limb into the socket 108 causing discomfort or injury to a wearer of the prosthetic device 100. Additionally, at least one implementation of the present disclosure provides an elevated vacuum solution that adapts to a residual limb during normal use. In particular, as a user walks and moves through normal daily routines a vacuum device can maintain a strong vacuum connection between a socket 108 and a liner 112.

In addition to providing a pathway for an elevated vacuum, at least one implementation of the present disclosure can provide a mechanical connection between the socket 108 and the liner 112. As noted, the pin 110 depicted in FIG. 3-5 may define a smooth outer surface. When inserted into the receiving port 312 the pin 110 can be squeezed by a locking plate 500 that locks the pin 110 into place. The locking plate 500 can comprise a washer shape that includes an internal radius through which the pin 110 passes. For example, the locking plate 500 can be configured such that when the pin 110 is withdrawn from the receiving port 312, the locking plate 500 can bias to one side causing the internal radius of the locking plate 500 to squeeze the pin 110.

Locking the pin 110 into the locking mechanism 310 in this way can further increase the connection and proprioception between a residual limb and the prosthetic device 100. Similarly, in at least one embodiment, the pin 110 may comprise a ledged exterior (not shown) that is designed to interact with a ratchet-like device within the locking mechanism 310. One will understand that several different methods are known in the art for locking a pin 110 within a locking mechanism 310 and that a variety of these methods can incorporate a pin 110 comprising vacuum channels as disclosed within this application.

FIG. 5 also depicts a pin release button 520 that allows the pin 110 to be easily removed from the receiving port 312. The pin release button 520 can function by removing pressure from the locking plate 500 such that the locking plate 500 no longer squeezes the pin 110. The pin release button 520 may also expose the interior of the socket 108 to the atmosphere destroying any vacuum present within the socket 108. One will understand that destroying the vacuum within the socket 108 and providing a button to release the pin 110 can make it much easier for a prosthetic device wearer to doff a prosthetic device.

The flange 420 of the pin 110 preferably extends around the circumference of the pin 110. The flange 420 can extend far enough that it substantially covers the opening of the receiving port 312 when the pin 110 is inserted into the receiving port 312 (shown in FIG. 5). The flange 420 is preferably located above the at least one passageway 302 to effectively seal and allow for expulsion of air.

The opening of the receiving port 312 may comprise an inverted conical shape 320. The inverted conical shape 320 may allow the pin 110 to be easily guided into the receiving port 312, while the flange 420 may prevent the pin 110 from being inserted too deeply into the receiving port 312. The annular flange 420 is preferably located proximally to the at least one passageway 302 and the conical opening 320. The annular flange 420 has an edge profile 422 adapted to correspondingly mate with a surface of the receiving port 312 defining the conical opening 320.

The flange 420 may prevent the vacuum from being applied to the interior of the socket 108 when the pin 110 is completely inserted into the receiving port 312. For example, when a wearer of the prosthetic device 100 places weight on the socket 108, the flange 420 may partially seal the at least one passageway 302 from the interior of the socket 108 preventing the vacuum from being applied to the interior of the socket 108. In this and similar embodiments the vacuum can be applied to the interior of the socket 108 when the wearer of the prosthetic device 100 is not weighting the prosthetic device 100, for example, while walking.

A method for expelling air in the prosthetic device 100 with a vacuum assisted suspension system places the suspension liner 112 into the socket 108 and orients the pin 110 with the receiving port 312. Then the pin 110 is inserted into the receiving port 312 such that air between the socket 108 and the suspension liner 110 is expelled at least through the passageway 302 into the bore 300 and through channel 314 to an exterior of the locking mechanism 310. The annular flange 420 defined by the pin rests at a proximal area above the at least one passageway 302 against a proximal end of the locking mechanism 310 when the pin 110 is fully received by the receiving port 312.

The method further includes sealing an outer surface 428 of the pin 110 against the side wall 315 defining a cavity 313 of the receiving port 312. The locking mechanism 310 may include the first and second seals 410, 510 protruding inwardly into the cavity 313 from the side wall 315 and is adapted to engage the outer surface 428 of the shaft 426. Air may be expelled from the side wall 315 via at least one release port 400 as the pin 110 is inserted into the cavity 313.

Accordingly, FIGS. 1-5 provide a number of components, schematics, and mechanisms for using vacuum tunnels within a pin 110 and locking mechanism 310 to create an elevated vacuum within a prosthetic device 100. In particular, embodiments of the present disclosure provide the ability to apply a vacuum force to the socket 108 only when a user has nearly completed donning the socket 108. Applying the vacuum force at this point may provide the benefit of not sucking a residual limb into the socket 108 in a way that can cause discomfort and/or injury. One will understand, however, that in light of the above disclosure it is apparent that implementations of the present disclosure exist that can apply a vacuum force through the pin 110 and locking mechanism 310 at any time —for example, before a user has inserted his or her residual limb into the socket 108.

Figures 6A, 6B, 6C:
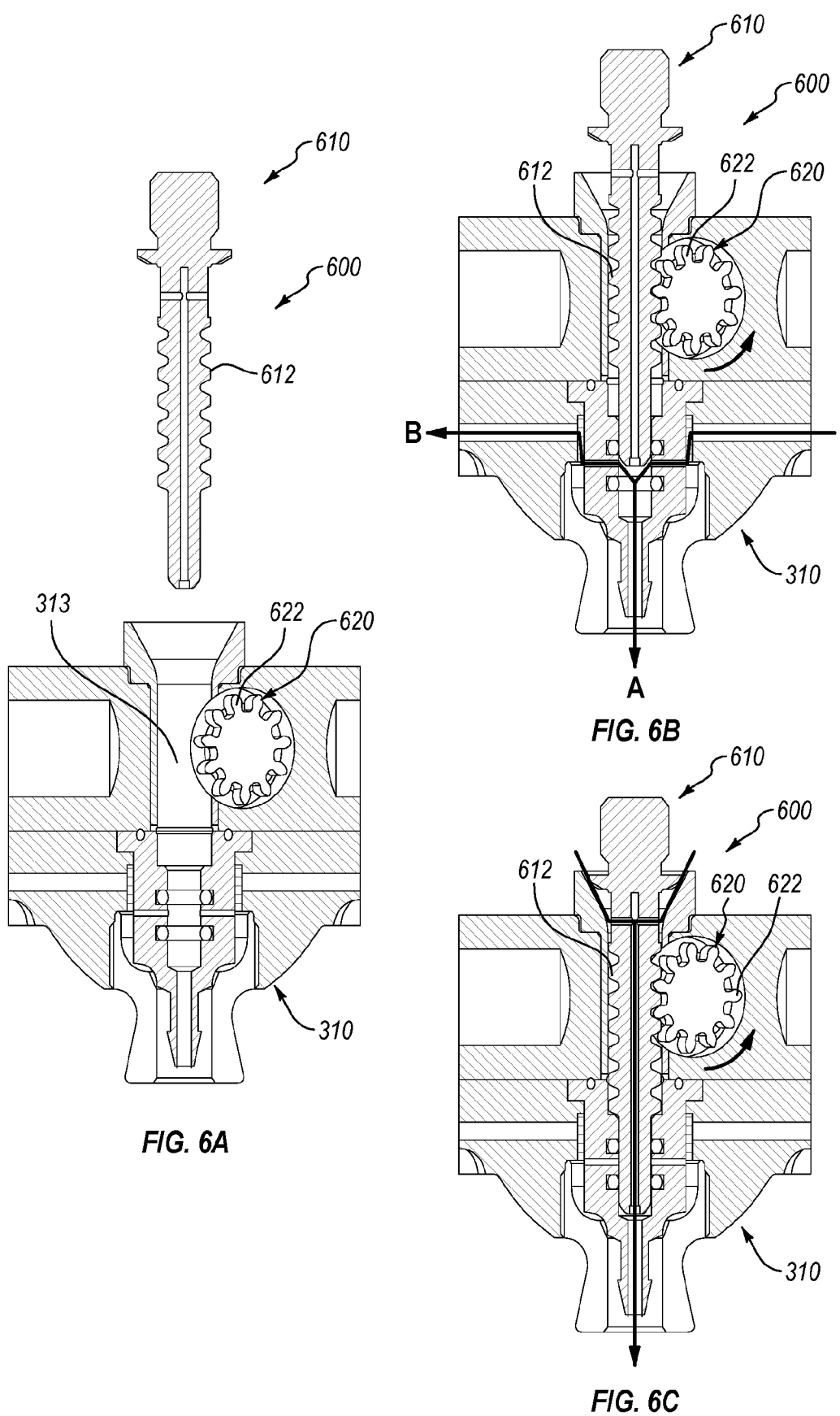
FIGS. 6A-6C show another embodiment of the prosthetic device and installation thereof.

Referring to FIGS. 6A-6C, another embodiment 600 includes a pin 610 defining a plurality of teeth 612 formed along an exterior surface thereof. The teeth 612 may be circumferentially formed about the pin 610 and may define a "rack" for engagement with teeth 622 of a pinion 620 supported by the locking mechanism 310. The pinion 620 is arranged to rotate as the pin 610 is inserted into the locking mechanism 310 through the cavity 313. The pinion 620 may be arranged so as to only rotate in a single direction when the pin 610 engages the pinion 620. The pinion 620 may be disengaged by suitable means from the pin 610 in order to permit withdrawal of the pin 610 from the locking mechanism 310. The remainder of the locking mechanism 310 may resemble the embodiment of FIGS. 1-5.

Turning to FIGS. 7A-7C, yet another embodiment 700 has a pin 710 defining a plurality of teeth 712 suitably angled to permit one-way engagement with teeth 722, 724 of a detent mechanism 720 biased into an middle portion 726 of the cavity 313. The detent 722, 724 may be formed unitarily and engaging the plurality of 712 from opposed directions, or the detent 722, 724 may be formed circumferentially. The detent mechanism 720 may be spring-loaded by a spring 728 so the detent 722, 724 is biased toward the pin 710 and the pin 710 is prevented from being withdrawn from the cavity 313. When desired, the detent mechanism 720 may be disengaged from the pin 710 by suitable means permitting removal of the detent 722, 724 from the pin 710 against the spring 728. The remainder of the locking mechanism 310 may resemble the embodiment of FIGS. 1-5.

The embodiments described may be used with a pressure regulator to insure the safety and comfort of the user, which may be achieved using mechanical and/or electronic methods known in the industry.

While the foregoing embodiments have been described and shown, alternatives and modifications of these embodiments, such as those suggested by others, may be made to fall within the scope of the disclosure. The principles described may be extended to other types of prosthetic or orthopedic devices.

The invention claimed is:

1. A pin lock for a prosthetic device in a vacuum assisted suspension system, comprising:
   a pin defining a longitudinally elongate bore and at least one passageway extending obliquely relative to the bore and communicating therewith at a proximal end of the pin;
   a locking mechanism having a receiving port arranged to receive the pin and a channel located at a distal end of the receiving port and adapted to communicate with the bore to exhaust air through the pin;
   wherein the pin defines teeth formed along an exterior surface thereof and arranged for engagement with a locking element of the locking mechanism;
   wherein the receiving port defines an elongated cavity arranged to receive the pin, the locking mechanism forming at least one release port located along the cavity and communicating to an exterior of the locking mechanism to expel air therefrom.

2. The pin lock of claim 1, wherein the teeth of the pin are circumferentially formed about the pin.

3. The pin lock of claim 1, wherein the locking element includes a pinion having corresponding teeth arranged for engagement with the teeth of the pin.

4. The pin lock of claim 3, wherein the pinion is arranged to rotate as the pin is inserted into the receiving port of the locking mechanism.

5. The pin lock of claim 3, wherein the pinion is arranged to rotate in a single direction when the pin engages the pinion.

6. The pin lock of claim 3, wherein the pinion is disengageable from the pin to permit withdrawal of the pin from the locking mechanism.

7. The pin lock of claim 1, wherein the locking element includes a detent mechanism biased into a middle portion of the receiving port for engagement with the teeth of the pin.

8. The pin lock of claim 7, wherein the teeth of the pin are angled to permit one-way engage with the detent mechanism.

9. The pin lock of claim 7, wherein the detent mechanism is spring-loaded by a spring such that the detent is biased toward the pin and the pin is prevented from being withdrawn from the receiving port.

10. The pin lock of claim 1, wherein the pin defines an annular flange protruding from a proximal area and a shaft extending distally from the annular flange, the bore being formed concentric with the shaft and the annular flange is entirely located above and proximally to the at least one passageway.

11. The pin lock of claim 10, wherein the annular flange is arranged to rest against the locking mechanism when the shaft is fully received by the receiving port.

12. The pin lock of claim 10, wherein the receiving port defines a conical opening narrowing distally toward the cavity adapted to closely receive the shaft.

13. The pin lock of claim 10, wherein the receiving port defines a conical opening, the annular flange having an edge profile adapted to correspondingly mate with a surface of the receiving port defining the conical opening to seal thereagainst.

14. The pin lock of claim 1, wherein the locking mechanism includes a first seal protruding inwardly into the cavity from a side wall defining the cavity and adapted to engage an outer surface of the shaft.

15. The pin lock of claim 1, wherein the at least one release port extends generally perpendicularly to a longitudinal length of the cavity.

16. The pin lock of claim 14, wherein the first seal is located distally to the at least one release port.

17. The pin lock of claim 16, further comprising a second seal protruding inwardly into the cavity from the side wall and adapted to engage the outer surface of the shaft, the second seal located proximally to the first seal and spaced a distance apart from the first seal and the at least one release port.

18. A method for expelling air in a prosthetic device with a vacuum assisted suspension system, the prosthetic device having a suspension liner carrying a pin at a distal end, the pin defining a longitudinally elongate bore and at least one passageway extending obliquely relative to the bore and communicating therewith at a proximal end of the pin, the prosthetic device further including a socket adapted to receive the suspension liner and comprising a locking mechanism having a receiving port and a channel located at a distal end of the receiving port, the method comprising:

placing the suspension liner into the socket and orienting the pin with the receiving port;

inserting the pin into the receiving port such that air between the socket and the suspension liner is expelled at least through the passageway into the bore and through channel to an exterior of the locking mechanism;

wherein the pin defines teeth formed along an exterior surface thereof and arranged for engagement with a locking element of the locking mechanism, the method further comprising the step of engaging the locking element with the teeth of the pin.

19. A pin lock for a prosthetic device in a vacuum assisted suspension system, comprising:

a pin defining a longitudinally elongate bore and at least one passageway extending obliquely relative to the bore and communicating therewith at a proximal end of the pin, the pin defining an annular flange at a proximal end entirely above the at least one passageway and a shaft extending distally from the annular flange, the bore being concentric with the shaft and an outer surface of the shaft defining a plurality of teeth;

a locking mechanism having a receiving port arranged to receive the pin and a channel located at a distal end of the receiving port and adapted to communicate with the bore to exhaust air through the pin therefrom, the receiving port defining an elongate cavity adapted to closely receive the shaft, the locking mechanism including a locking element arranged for extending into the cavity and selectively engaging the teeth of the pin;

wherein the locking mechanism forms at least one release port located along the cavity and communicating to an exterior of the locking mechanism to expel air therefrom.

\* \* \* \* \*